United States Patent
Yoon et al.

(10) Patent No.: US 9,895,558 B2
(45) Date of Patent: Feb. 20, 2018

(54) VOXEL TYPE BLOCK PHANTOM FOR A MULTIFUNCTIONAL RADIATION MEASUREMENT APPARATUS

(71) Applicant: THE CATHOLIC UNIVERSITY OF KOREA INDUSTRY-ACADEMIC COOPERATION FOUNDATION, Seoul (KR)

(72) Inventors: Do Kun Yoon, Gyeonggi-do (KR); Joo Young Jung, Gyeonggi-do (KR); Tae Suk Suh, Seoul (KR)

(73) Assignee: THE CATHOLIC UNIVERSITY OF KOREA INDUSTRY—ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/118,625

(22) PCT Filed: Jan. 29, 2015

(86) PCT No.: PCT/KR2015/000961
§ 371 (c)(1),
(2) Date: Aug. 12, 2016

(87) PCT Pub. No.: WO2015/122637
PCT Pub. Date: Aug. 20, 2015

(65) Prior Publication Data
US 2017/0043186 A1   Feb. 16, 2017

(30) Foreign Application Priority Data
Feb. 13, 2014  (KR) ........................ 10-2014-0016844

(51) Int. Cl.
*A61N 5/10* (2006.01)

(52) U.S. Cl.
CPC .... *A61N 5/1075* (2013.01); *A61N 2005/1076* (2013.01)

(58) Field of Classification Search
CPC .... A61B 6/583; A61N 5/1048; A61N 5/1071; A61N 5/1075; A61N 2005/1076
(Continued)

(56) References Cited

U.S. PATENT DOCUMENTS

| | | | | |
|---|---|---|---|---|
| 4,816,762 | A | * | 3/1989 | Bohning ................ G01R 33/58 324/300 |
| 5,506,884 | A | * | 4/1996 | Goodenough .......... G01T 1/169 250/252.1 |

(Continued)

FOREIGN PATENT DOCUMENTS

| | | |
|---|---|---|
| JP | 2003-240858 | 8/2003 |
| KR | 10-2009-0081883 | 7/2009 |

(Continued)

*Primary Examiner* — David Porta
*Assistant Examiner* — Blake Riddick
(74) *Attorney, Agent, or Firm* — Allen, Dyer, Doppelt + Gilchrist, P.A., Attorneys at Law

(57) ABSTRACT

The present invention relates to a voxel-type block phantom for a multifunctional radiation measurement apparatus. A phantom, for adjusting an amount of radiation, has solid pixel blocks, having a radiation measuring device equipped therein and different media and densities from one another, assembled on top of one another so as to be assembled into a 3-dimensional voxel, wherein the phantom is formed by placing a solid block which is appropriate for a density that corresponds to each pixel of the 3-dimensional voxel. An inspector can personally and instantly customize a phantom that is appropriate for a subject to be measured and thus can obtain an accurate measurement value.

4 Claims, 3 Drawing Sheets

(58) Field of Classification Search
USPC ......... 250/474.1, 370.07, 252.1; 378/207, 18
See application file for complete search history.

(56) References Cited

U.S. PATENT DOCUMENTS

| | | | | |
|---|---|---|---|---|
| 2003/0007601 A1* | 1/2003 | Jaffray | ................... | A61B 6/032 378/65 |
| 2005/0077459 A1* | 4/2005 | Engler | ................. | A61N 5/1048 250/252.1 |
| 2006/0027756 A1* | 2/2006 | Thomson | ................ | G01T 1/026 250/370.07 |
| 2007/0140413 A1* | 6/2007 | Saracen | ................... | A61B 6/08 378/18 |
| 2009/0236510 A1* | 9/2009 | Lacroix | ..................... | G01T 1/02 250/252.1 |
| 2012/0207283 A1* | 8/2012 | Muller | ................... | A61B 6/583 378/207 |
| 2013/0292580 A1* | 11/2013 | Schubert | ............. | A61N 5/1048 250/395 |
| 2015/0085993 A1* | 3/2015 | Scheib | ................. | A61N 5/1075 378/207 |
| 2016/0278734 A1* | 9/2016 | Hong | ..................... | A61B 6/583 |

FOREIGN PATENT DOCUMENTS

| | | |
|---|---|---|
| KR | 10-2013-0059668 | 6/2013 |
| KR | 10-2013-0106907 | 10/2013 |

\* cited by examiner

VOXEL TYPE BLOCK PHANTOM FOR A MULTIFUNCTIONAL RADIATION MEASUREMENT APPARATUS

TECHNICAL FIELD

The present invention relates to a voxel type block phantom for a multifunctional radiation measurement apparatus and, more particularly, to a voxel type block phantom for a multifunctional radiation measurement apparatus, which is capable of measuring a radiation absorbed dose passing through each of solid blocks when measuring a radiation beam in such a way as to configure the pixelated solid blocks having several media and densities in a voxel type by combining the solid blocks in layers.

BACKGROUND ART

All of radiotherapy devices are designed to be checked regular intervals whether a precise radiation dose reaches a target point by taking into consideration stability and reappearance. Today, when a radiation beam is measured using such a radiotherapy device, a water phantom and a solid water-equivalent phantom are chiefly used with the recommendation of International Atomic Energy Agency (IAEA).

In general, the measurement of radiation is performed for quality assurance (QA) of the measurement of radiation by taking into consideration the volume of a radiotherapy patient and the location of a tumor. The number of beams radiated is many and has many angles. However, such conventional equipment has a difficulty in accurate measurement in the recent scheme that requires precision and complexity. More specifically, if a non-uniformity medium, such as air or a bone, is included in an object whose radiation will measured, corresponding copying is difficult and it is also difficult to insert a measurement unit. In order to implement a non-uniformity medium, a specially produced phantom is used in some organs, but there is a problem in that even an opportunity cost given up due to the use of the specially produced phantom is included in addition to a cost.

Today, a phantom used in a radiotherapy-related task site needs to be fabricated according to a single measurement target and to be used for only such a purpose. That is, it is difficult to use a conventional single phantom for various purposes for measurement targets which have different various media and have different densities even in portions within one medium.

DISCLOSURE

Technical Problem

The present invention has been made to solve the above problems occurring in the prior art and has been made keeping in mind the form of a block toy with which children play, and an object of the present invention is to provide a voxel type block phantom for a multifunctional radiation measurement apparatus, wherein a testee person can customize the voxel type block phantom by combining several solid blocks having different media and densities in a three-dimensional manner so that the solid blocks can be used for various phantoms suitable for an object of a radiation measurement target.

Technical Solution

In order to achieve the above object, in a voxel type block phantom for a multifunctional radiation measurement apparatus according to the present invention, in a phantom for controlling a radiation dose, wherein pixelated solid blocks, each having a radiation measurement unit embedded therein and having different media and densities, are combined in layers and assembled in a three-dimensional voxel type, and solid blocks, each suitable for density corresponding to each of the three-dimensional voxel type pixels, are disposed to form the phantom.

Furthermore, an insertion groove having the radiation measurement unit embedded therein is formed in the top surface of the solid block, and a cover covering the insertion groove is provided at the top surface. The phantom further includes a concave-convex portion having a groove and a protrusion in the outside surface of the solid block in order to combine the solid blocks in layers.

Furthermore, in the three-dimensional voxel type of the pixelated solid blocks having different densities, the solid blocks corresponding to the respective pixels may be disposed with reference to a diagnostic image including anatomical information.

Advantageous Effects

In accordance with the voxel type block phantom for a multifunctional radiation measurement apparatus according to the present invention, there are advantages in that a testee person can instantly customize a phantom suitable for a use of a measurement target and a corresponding precise measurement value can be derived.

Furthermore, there are advantages In that a phantom can be modified and added, if necessary, because it is produced by stacking the phantom like a block and a corresponding different radiation measurement value can be obtained. A conventional phantom derives a fixed measurement value with. respect to a regularized phantom. In contrast, the phantom of the present invention. has an advantage in that various forms of measurement values can be derived, if necessary, according to a testee's need.

Furthermore, it is expected that a significant cost reduction effect can be achieved from a point of view of researchers and hospital testees because utilization versus a product cost is much cheaper than that of a conventional phantom system in which hospitals or researchers individually purchase phantoms suitable for their uses.

MODE FOR INVENTION

Hereinafter, preferred embodiments of a voxel type block phantom for a multifunctional radiation measurement apparatus according to the present invention are described in detail with reference to the accompanying drawings. The present invention is not limited to the disclosed embodiments, but may be implemented in various different ways. The present embodiments are provided to only complete the disclosure of the present invention and to allow a person having ordinary skill in the art to completely understand the category of the invention.

Figure 1:
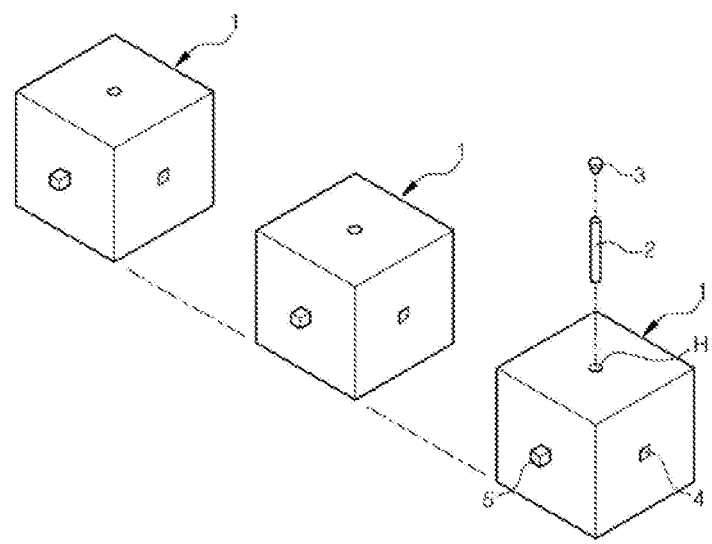
FIG. 1 is a perspective view of a solid block used in a voxel type block phantom according to the present invention.

FIG. 1 is a perspective view of a solid block used in a voxel type block phantom according to the present invention.

As shown in FIG. 1, the solid block 1 used in the voxel type block phantom according to the present invention includes a plurality of the same regular hexahedron or regular hexagon forms having various media and densities. An insertion groove H connected to the inside of the solid block is formed in the top surface of each of the plurality of solid blocks 1. In order to correct a radiation attenuation effect attributable to the insertion groove H after a very small radiation measurement unit 2 is inserted into the insertion groove H, a cover formed to cover the insertion groove H in a screw coupling manner. For example, the cover 3 may be coupled to the insertion groove H through screw coupling by forming a screw thread on the upper side of the inside of the insertion groove H and forming a screw thread in the circumference of the lower side of the cover 3, but the cover 3 and the insertion groove H may be coupled in various ways in addition to the screw coupling.

Furthermore, a concave-convex portion having an engraved groove 4 and an embossed protrusion 5, such as that formed in a toy block, is formed in the outside surface of each of the solid blocks 1 so that the solid blocks can close adhere to each other and can be combined. Accordingly, the protrusion 5 is inserted into the groove 4. That is, the solid blocks are stacked in layers and connected by combining the grooves 4 and protrusions 5 of the concave-convex portions together as if the toy blocks are piled up.

The voxel type block phantom of the present invention itself can be copied using the sold blocks 1 having such a structure.

Figure 2:
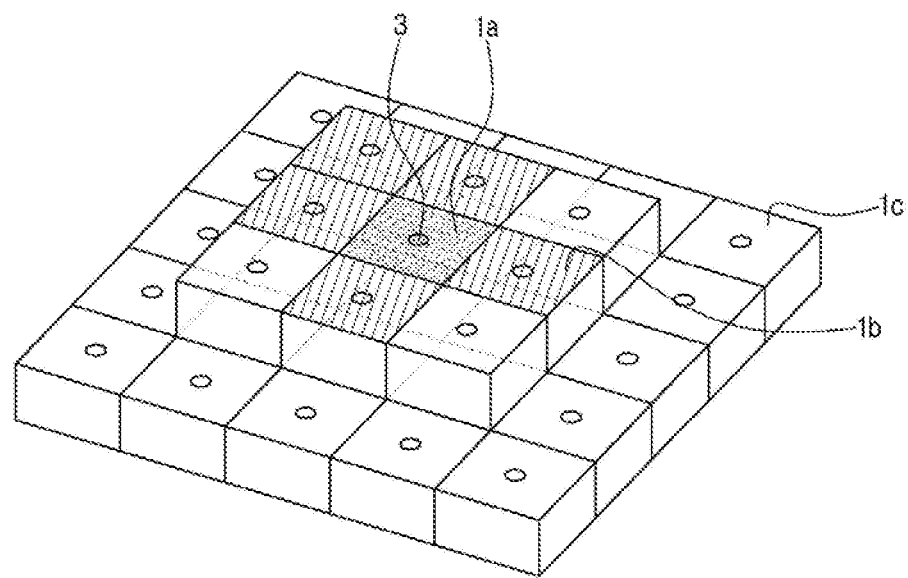
FIG. 2 is a perspective view of the voxel type block phantom according to the present invention showing the shape in which solid blocks are combined in a single layer.

FIG. 2 is a perspective view of the voxel type block phantom according to the present invention showing the shape in which the solid blocks are combined in a single laver.

For example, in the case of a diagnostic image including anatomical information about the head of a person, if the diagnostic image is divided like corresponding pixels, a solid block having a medium and density corresponding to each pixel is selected, and such solid blocks are combined and stacked through the grooves 4 and protrusions 5 of the concave-convex portions of the solid blocks 1 shown in FIG. 1, a phantom capable of copying one image having a two-dimensional manner, such as an image shown in FIG. 2, is obtained. That is, an image of a yellow solid block 1a at the center, images of pink solid blocks 1b around the yellow solid block 1a, and images of deep blue solid blocks 1c in the outer wall, which have different media and densities, are divided, combined, and stacked as shown in FIG. 2. Before the solid blocks 1a, 1b, and 1c are combined and stacked, the radiation measurement unit 2 for radiation measurement is inserted into the insertion groove H of the solid block 1 shown in FIG. 1 and is cover and sealed by the cover 3. The diagnostic image may be a CT image captured by a CT testing device or an MR image captured by an MRI testing device.

Figure 3:
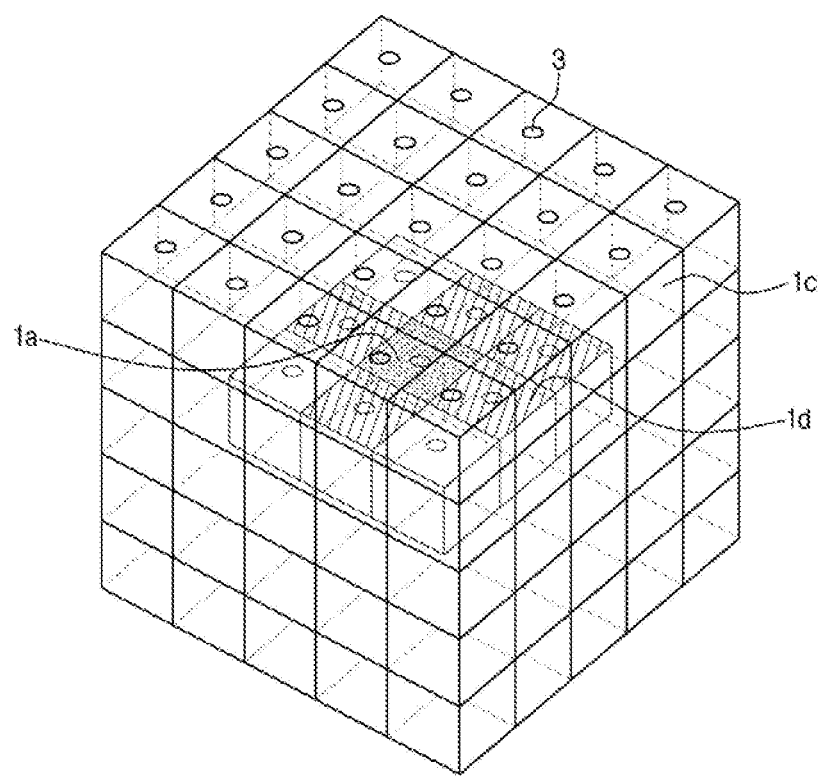
FIG. 3 is a perspective view of the state in which the voxel type block phantom according to the present invention is used.
Figure 4:
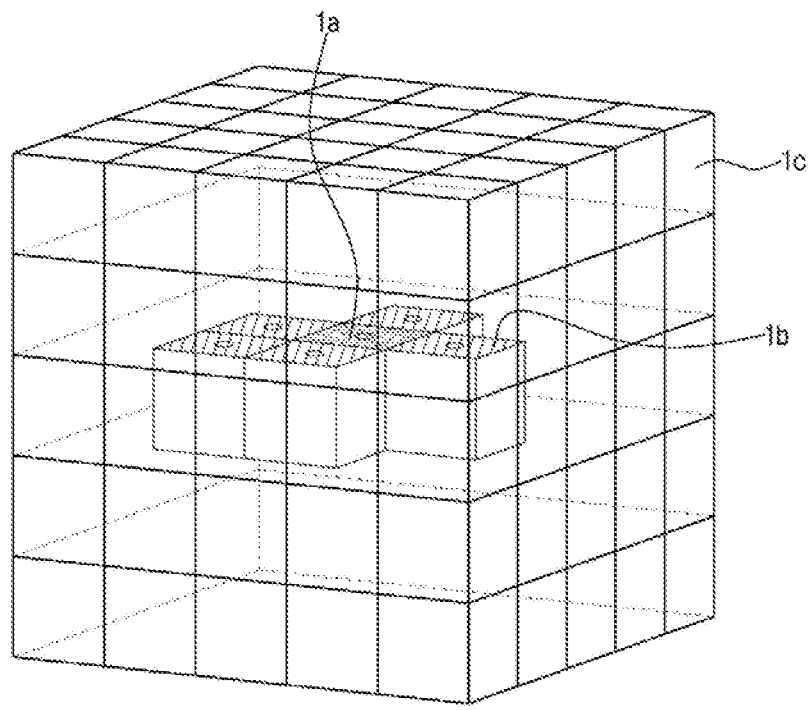
FIG. 4 is a perspective view of the state in which the voxel type block phantom according to the present invention is used, which is viewed at a different angle.

FIG. 3 is a perspective view of the state in which the voxel type block phantom according to the present invention is used, and FIG. 4 is a perspective view of the state in which the voxel type block phantom according to the present invention is used, which is viewed at a different angle.

As shown in FIGS. 3 and 4, if the solid blocks 1a, 1b, and 1c are combined and stacked in a two-dimensional manner using the above method and are then attached in multiple layers in a required form, a stereoscopic three-dimensional phantom is completed and can be used for various purposes. Solid blocks placed in respective pixels within the stereoscopic three-dimensional phantom as described above are placed as the solid blocks 1a, 1b, 1c having different media and densities depending on the medium and density of a measurement target as described above.

The media and densities having such a difference have been described above, but are divided into different solid block images in different colors in the drawings. For example, in the case of images of the phantoms shown in FIGS. 3 and 4, an image of the solid block 1a at the center is displayed in yellow, images of the solid blocks 1b around the image of the yellow solid block 1a are displayed in pink, and images of all the solid blocks 1c other than the yellow and pink solid blocks 1a and 1b are displayed in gray in order to indicate a difference between different media and densities. If a measurement target is changed and thus a medium and density according to the location of each pixel are changed, only a solid block changed in response to the change is disposed again and modified or a corresponding solid block is additionally disposed. Furthermore, in the case of a measurement target having a quite different medium and density depending on the location of each pixel, the location of each solid block corresponding to the pixel is designed and stacked again. Accordingly, a phantom having a different medium and density for each pixel suitable for a measurement target using a single solid block is configured in various ways.

Although the voxel type block phantom for a multifunctional radiation measurement apparatus according to the present invention has been described above with reference to the illustrated drawings, the present invention is not limited to the embodiments and drawings disclosed in this specification, but may be modified in various ways by those skilled in the art without departing from the technical spirit of the present invention.

SEQUENCE LIST TEXT

| | |
|---|---|
| 1, 1a, 1b, 1c: solid block | |
| 2: radiation measurement unit | |
| 3: cover | 4: groove |
| 5: protrusion | H: insertion groove |

The invention claimed is:

1. A phantom for controlling a radiation dose, the phantom comprising:
   a plurality of pixelated solid blocks, each pixelated solid block having a radiation measurement unit embedded therein and having different media and densities,
   said plurality of pixelated solid blocks being combined in layers and assembled in a three-dimensional voxel type shape,
   each of said plurality of pixelated solid blocks being suitable for density corresponding to each of a plurality of three-dimensional voxel type pixels in the three-dimensional voxel type shape.

2. The phantom of claim 1, wherein each pixelated solid block defines an insertion groove extending inwardly from an external surface thereof; wherein the insertion groove is carrying said radiation measurement unit therein; and wherein each pixelated solid block comprises a cover covering the insertion groove at the external surface.

3. The phantom of claim 1, wherein each pixelated solid block has opposing first and second external surfaces defining a tongue and groove arrangement for combining adjacent pixelated solid blocks in the three-dimensional voxel type shape.

4. The phantom of claim 1, wherein the three-dimensional voxel type shape is based upon a diagnostic image comprising anatomical information.

* * * * *